United States Patent
Elliott et al.

(10) Patent No.: US 9,759,534 B2
(45) Date of Patent: Sep. 12, 2017

(54) ARROW OR BOLT HAVING A CHEMICAL SHOT INDICATOR

(71) Applicants: Deane Owen Elliott, Woodbridge, VA (US); Mark Rogers Davidson, Florahome, FL (US)

(72) Inventors: Deane Owen Elliott, Woodbridge, VA (US); Mark Rogers Davidson, Florahome, FL (US)

( * ) Notice: Subject to any disclaimer, the term of this patent is extended or adjusted under 35 U.S.C. 154(b) by 0 days.

(21) Appl. No.: 15/261,002

(22) Filed: Sep. 9, 2016

(65) Prior Publication Data

US 2017/0074628 A1 Mar. 16, 2017

Related U.S. Application Data

(60) Provisional application No. 62/217,059, filed on Sep. 11, 2015.

(51) Int. Cl.
*F42B 6/04* (2006.01)
*F42B 12/36* (2006.01)
*G01N 33/84* (2006.01)

(52) U.S. Cl.
CPC .............. *F42B 12/362* (2013.01); *F42B 6/04* (2013.01); *G01N 33/84* (2013.01)

(58) Field of Classification Search
CPC ................................. F42B 6/04; F42B 12/362
USPC .................................................. 473/578, 581
See application file for complete search history.

(56) References Cited

U.S. PATENT DOCUMENTS

| | | | | |
|---|---|---|---|---|
| 3,150,875 A * | 9/1964 | Searles | ..................... | F42B 6/04 102/334 |
| 4,277,069 A * | 7/1981 | Rouse | ..................... | F42B 6/04 473/581 |
| 5,035,435 A * | 7/1991 | Burgeson | ................. | F42B 6/04 239/34 |
| 6,186,913 B1* | 2/2001 | Thomas | ................ | F42B 12/362 473/581 |
| 6,238,310 B1* | 5/2001 | Morrison | ................. | F42B 6/04 473/581 |
| 6,641,493 B1* | 11/2003 | Shifflett | .................... | F42B 6/04 473/578 |
| 7,426,888 B2* | 9/2008 | Hunt | ........................ | F42B 6/04 102/513 |
| 7,488,267 B2* | 2/2009 | Hunt | ........................ | F42B 6/04 473/578 |
| 7,775,919 B2* | 8/2010 | Oswald | ..................... | F41H 3/00 428/919 |

(Continued)

*Primary Examiner* — Alexander Niconovich
(74) *Attorney, Agent, or Firm* — Patent Law Associates

(57) ABSTRACT

An arrow or bolt comprising of an indicator that will chemically indicate the fluids that have come into contact with the arrow as it has passed through the animal. The indicator may comprise a treated substrate that chemically reacts with bodily fluids of the animal as the arrow or bolt passes through the animal to provide an indication of the acidity thereof. The chemical indicator may be attached to the arrow allowing a user to reuse the arrow by simply removing a used indicator and replacing with an unused chemical indicator. Alternatively, a portion of the arrow or bolt may be provided with an absorptive neutral substrate on which a reusable chemical indicator dye could be applied. The substrate could be cleaned following use and the indicator dye reapplied to enable reuse of the arrow or bolt.

18 Claims, 3 Drawing Sheets

(56) References Cited

U.S. PATENT DOCUMENTS

| | | | | |
|---|---|---|---|---|
| 7,914,406 B2* | 3/2011 | Andrews | ............ | F42B 6/06 |
| | | | | 473/578 |
| 8,152,663 B2* | 4/2012 | Grundman | ............ | F42B 6/04 |
| | | | | 473/578 |
| 9,121,678 B1* | 9/2015 | Kendall | ............ | F42B 12/362 |
| 9,335,136 B1* | 5/2016 | Campbell | ............ | F42B 12/362 |
| 9,366,513 B1* | 6/2016 | Kendall | ............ | F42B 12/362 |
| 2002/0028718 A1* | 3/2002 | Coe | ............ | F42B 6/06 |
| | | | | 473/586 |
| 2008/0176683 A1* | 7/2008 | Marshall | ............ | F42B 6/06 |
| | | | | 473/586 |

* cited by examiner

ARROW OR BOLT HAVING A CHEMICAL SHOT INDICATOR

CROSS-REFERENCE TO RELATED APPLICATIONS

This application claims the benefit of priority of U.S. Provisional Application 62/217,059, filed Sep. 11, 2015.

BACKGROUND OF THE INVENTION

The present invention relates generally to a hunting arrow or bolt and, more particularly, to a chemical indicator signifying whether a game animal was shot by the arrow or bolt.

In archery hunting, shot placement is very critical to ensuring a quick and humane kill. Archers practice for hours to make sure they make ethical shots when hunting. The most desired shot by an archery hunter is referred to as a "double lung" shot where the arrow or bolt passes through both lungs of an animal standing broadside to the hunter. With today's compound bow and crossbow technology, it is very difficult to determine where the arrow or bolt has gone once it leaves the bow or crossbow due to the speed that the projectile is traveling. Many crossbow bolts are traveling at velocities approaching 400 feet per second. The projectile velocity also means that the arrow or bolt frequently passes completely though the animal.

Archery hunters are generally physically close to their prey when taking a shot, generally forty yards or less. Deer may often sense a hunter's presence and be additionally alert. Deer often hear the release of the arrow from the bow before the arrow reaches them which allows them to initiate movement. This movement can affect the impact point of the arrow or bolt. A broadside shot when aimed can quickly become a quartering shot in which the arrow impacts the animal at an angle, either from the rear to the front or from the front to the rear, which may not be as lethal as the desired transverse double lung shot. Such quartering shots are more likely to result in an arrow passing at least partially through the animal's digestive tract.

Given the difficulty of observing the arrow during its flight to the target, hunters usually seek the arrow afterward in order to examine it for indications of the shot. An arrow having hit its target will be covered in blood and other fluids from having passed through the target animal.

U.S. Pat. No. 9,121,678 to Kendall discloses the use of a "blood ring" on an arrow which is a region that allows absorption of fluids as an arrow or bolt passes through an animal. This region may be provided with a textured surface for collecting blood that is then visually inspected by the hunter. A simple observation of the presence of blood does not provide any indication of whether the shot is a humane shot (e.g., double lung) or a gut shot in which the arrow or bolt passes through other portions of the animal.

Animal blood is generally neutral, having a pH in the range of 7.35 to 7.45. Shots passing through the animal's lungs would be exposed to primarily to blood. Digestive fluids in the animal's gut are highly acidic, generally having a pH ranging from 1 to 4.5. A shot passing thorough the animal's gut is likely to be exposed to digestive fluids in addition to blood. A variety of chemical compounds are known to exhibit color changes upon contact with fluids of various pH, specifically including color changes when contacting acidic fluids.

It would be advantageous to provide an indicator capable of detecting and indicating pH by a visible change in color that would provide an immediate indication of a gut shot that would permit the hunter to determine how the animal should be tracked. If an indicator shows that the animal has been hit in the stomach region (a gut shot), it is best for the hunter to back away and allow the animal to lay down and die rather than to pursue it immediately. When hunting deer, an animal that has been gut shot is often left to lay overnight if weather conditions allow so as not to jump it from its bedded location which can easily cause the wounded animal to travel as much as a mile before bedding down again. Conversely, if the indicator shows a clean, non-gut shot, has occurred, the hunter can begin tracking the animal in a normal practice of waiting a short time (one-half hour).

SUMMARY OF THE INVENTION

Accordingly, the present invention, in any of the embodiments described herein, may provide one or more of the following advantages:

It is an object of the present invention to provide an arrow comprising a region or section that will chemically indicate the fluids that have come into contact with the arrow as it has passed through the animal. The region or section may be comprised of litmus paper or a like material that reacts with bodily fluids of the animal as the arrow or bolt passes through the animal providing an indication of the acidity thereof.

It is a further object of the present invention to provide an arrow or bolt comprising a chemical indicator that may be attached to the arrow or bolt allowing a user to reuse the arrow or bolt by simply removing and replacing the chemical indicator. Alternatively, a portion of the arrow or bolt may be provided with an absorptive neutral carrier substrate on which a reusable chemical indicator dye having similar color indicating properties to litmus could be applied. The substrate could be cleaned and the reactive material reapplied after use to enable reuse of the arrow or the substrate could be replaced with a second treated substrate.

It is a still further object of the present invention to provide an arrow or bolt having a chemically sensitive portion for generally indicating the acidity of the bodily fluids through which the arrow or bolt has passed that is durable in construction, inexpensive of manufacture, carefree of maintenance, easily assembled, and simple and effective to use.

These and other objects of the present invention are fulfilled by an arrow or bolt comprising of an indicator that will chemically indicate the fluids that have come into contact with the arrow as it has passed through the animal. The indicator may comprise a treated substrate that chemically reacts with bodily fluids of the animal as the arrow or bolt passes through the animal to provide an indication of the acidity thereof. The chemical indicator may be attached to the arrow allowing a user to reuse the arrow by simply removing a used indicator and replacing with an unused chemical indicator. Alternatively, a portion of the arrow or bolt may be provided with an absorptive neutral substrate on which a reusable chemical indicator dye could be applied. The substrate could be cleaned following use and the indicator dye reapplied to enable reuse of the arrow or bolt.

BRIEF DESCRIPTION OF THE DRAWINGS

The advantages of this invention will be apparent upon consideration of the following detailed disclosure of the invention, especially when taken in conjunction with the accompanying drawings wherein.

DESCRIPTION OF THE PREFERRED EMBODIMENT(S)

Many of the fastening, connection, processes and other means and components utilized in this invention are widely known and used in the field of the invention described, and their exact nature or type is not necessary for an understanding and use of the invention by a person skilled in the art, and they will not therefore be discussed in significant detail. Also, any reference herein to the terms "forward" or "rearward" are used as a matter of convenience and are determined by the viewing in the direction of flight of the arrow. "Upward" and "downward" orientations are relative to the ground as are any references to "horizontal" or "vertical" planes. Furthermore, the various components shown or described herein for any specific application of this invention can be varied or altered as anticipated by this invention and the practice of a specific application of any element may already be widely known or used in the art by persons skilled in the art and each will likewise not therefore be discussed in significant detail. When referring to the figures, like parts are numbered the same in all of the figures.

Figure 1:
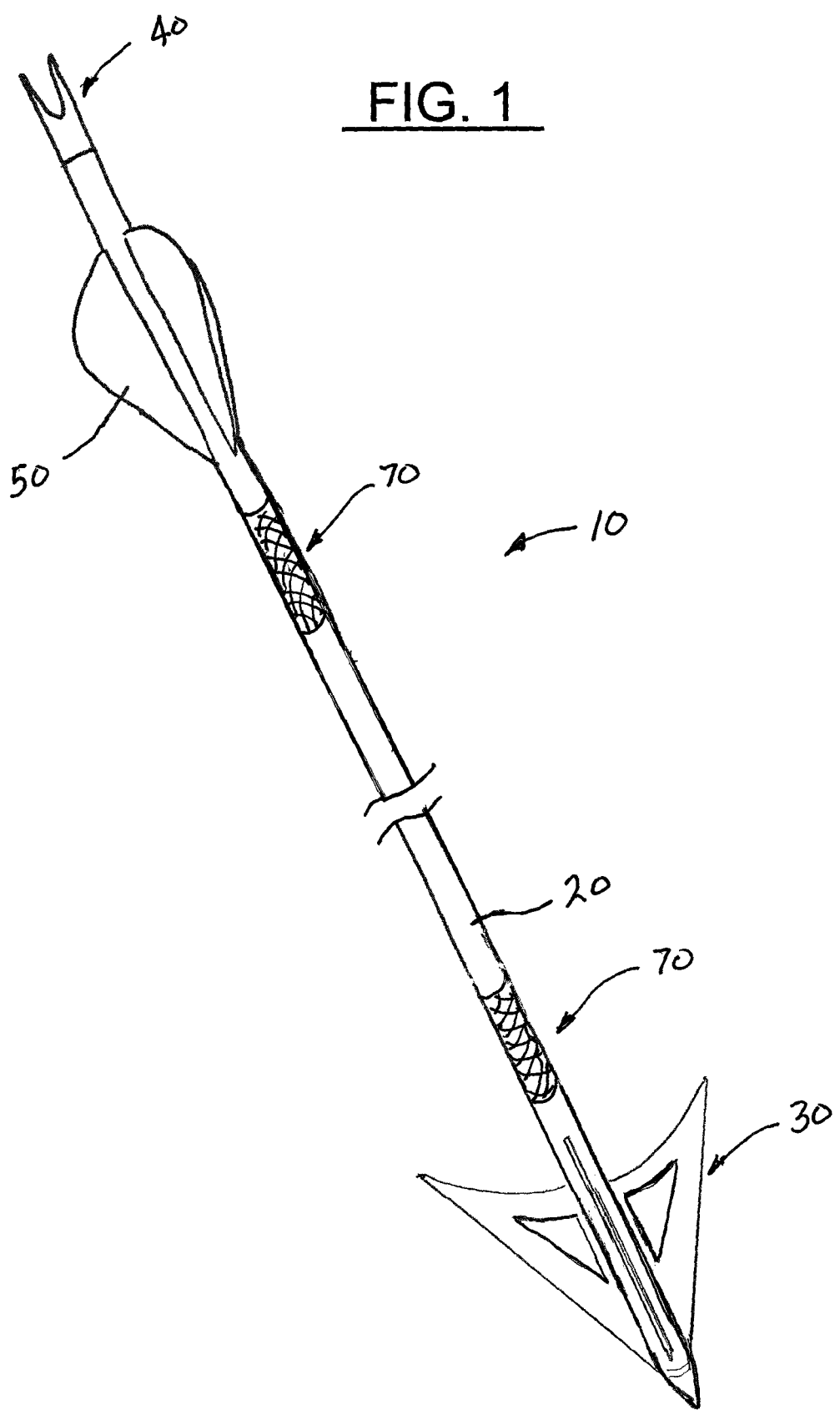
FIG. 1 illustrates an arrow incorporating one embodiment of the present invention.

Referring to FIG. 1 there is shown a traditional crossbow bolt or arrow 10 comprising an elongate shaft 20 having a broadhead tip 30 at one end and a traditional nock 40 for engaging the string of a crossbow or bow at the opposite end. Fletchings or vanes 50 may be attached to the shaft 20, typically proximate to the trailing end where the nock 40 is located, to guide the arrow 10 in flight.

At least one indicator 70 is affixed to the shaft 20 and longitudinally positioned between the tip 30 and the nock 40. The indicator 70 is configured to chemically react with fluids to which it is exposed and to provide a visual color change in the event that such fluids are acidic in nature (having a pH value less than 6), the color change being from a first color representing neutral acidity and a second color indicating exposure to acidic solutions. Multiple indicators 70 may be provided and spaced along the length of the shaft to provide redundancy in the shot indication.

As the arrow or bolt 10 passes through an animal's chest cavity, it interacts the bodily fluids therein. In the preferred broadside chest shot, the heart and/or lungs which contain mainly blood are primarily impacted. Animal blood is generally understood to have a generally neutral acidity with a pH in the range of 7.35 to 7.45. A pH of 7 is considered neutral. The indicator 70 is likely to be exposed only to the neutral blood in a broadside chest shot and will not exhibit a color change indicating exposure to acidic fluids. If the shot is off target or the animals moves such that the shot passes wholly or partially through the animal's digestive tract, the arrow is likely to be exposed to digestive fluids in addition to blood. The stomach pH of herbivores is typically around 4.5 (slightly acidic) while the stomach pH of carnivores and omnivores is typically between 1 and 3. An arrow 10 passing through the gut region of the animal will expose the indicator 70 to the more acidic fluids of the digestive tract causing the indicator to change appearance from the first color to the second color. In all instances, the arrow 10 of a missed shot would not contain any trace of bodily fluids from the animal. An arrow penetrating the animal will contain evidence of bodily fluid on the external surfaces, including the indicator, and fletching.

The indicator 70 comprises a substrate 72 that has been treated with an indicating dye that chemically reacts with acidic fluids causing the indicating dye and the treated substrate 72 to change color appearance. One substrate 72 is blue litmus paper which remains blue when exposed to the generally neutral pH blood but turns red when exposed to acidic fluids (e.g., fluids having a pH value of less than 5). Upon inspection after a broadside double-lung shot, a hunter noting the unchanged color of the indicator 70 can deduce that the shot was not a gut shot and the animal will not travel far from the location at which it was shot before succumbing to the wound. A hunter retrieving the arrow and observing that the indicator 70 has changed to the second color can deduce that the shot was a gut shot and that the animal may travel further from the location at which it was shot before succumbing to the wound, especially if the hunter attempts to locate the fallen animal. Deer have been known to run as much as a mile before succumbing to a gut shot.

The indicator substrate 72 may be replaced after use to prepare the arrow for the next shot. An adhesive 79 may be applied to the surface of the substrate that is adjacent to the shaft to affix it thereto. Replacing the indicator 70 is accomplished by removing the used indicator 70 and re-affixing a new indicator. A self-adhesive arrangement in which the adhesive is applied to the substrate 72 and a well-known peel-off protective cover applied to protect the adhesive until use enables the indicator 70 to be easily applied to any conventional arrow or bolt 10, removed following use, and replaced with a new indicator 70.

Figure 4:
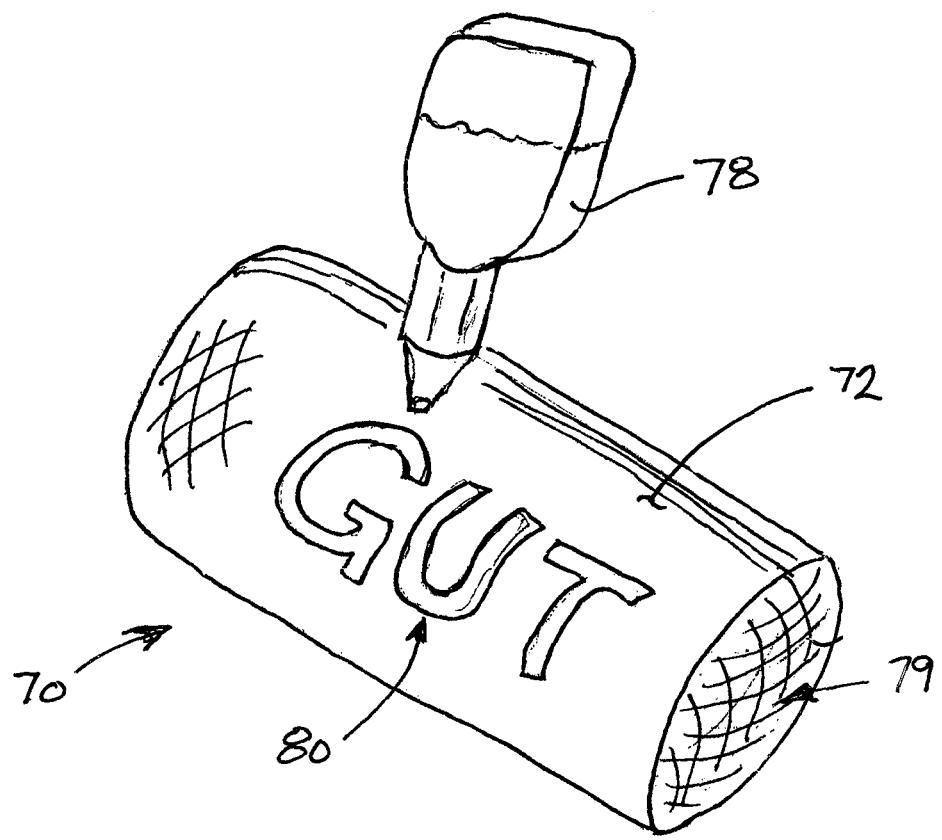
FIG. 4 illustrates an alternate shot indicator the present invention.

Alternatively, when referring to FIG. 1 in conjunction with FIG. 4, the indicator substrate 72 may be a neutral, absorbent material such as paper or fabric, that is treated with a chemical indicating dye 78 that chemically reacts with acidic solutions to exhibit a color change. The substrate may require treatment prior to use to assure it has a neutral or slightly basic pH that will not react with the indicator dye 78 prior to use on the arrow. Many paper-based materials are known to be slightly acidic in their readily available form. Pre-treating substrates with sodium bicarbonate (baking soda) has proven an effective way to neutralize paper substrates prior to application of the indicating dye.

The substrate 72 may then be affixed to the arrow shaft 20 for use as described above. The self-adhesive arrangement provided on the substrate enables the indicator 70 to be easily packaged and dispensed for use by archers who can then affix one of more indicators 70 on their arrows prior to use.

The arrow fletching 50 may also be configured to function as the indicator substrate 72 by selecting materials that retain sufficient chemical indicating dye 78 to exhibit the desired color change when exposed to digestive tract acids. In this configuration, the hunter would treat the flecthing 50 with the indicator dye 78 prior to use of the arrow and then examine the fletching for evidence of color change in the indicating dye on the fletching following the shot.

Chemical indicating dyes 78, referred to as halochromic chemical compounds, undergo color changes when exposed to varying pH levels or changes and allow the indicator 70 to function. One such indicating dye phenaphthazine yellow, also known as Nitrazine Yellow, which is blue in color under neutral conditions and changes to yellow/tan when exposed to acidic solutions. Another indicating dye is bromothymol sulfone phthalein, also known as bromothymol blue, which is also normally blue in color, but changes color to yellow when exposed to acidic fluids. These color changes are preferred as they provide contrast to the red color of the blood that is likely to be present on the indicator as well. Numerous other chemicals are known to exhibit color changes when exposed to acidic solutions and offer the ability to refine the range(s) of pH causing color change and even the resultant color, including lacmoids and methyl red. Other indicator dyes may also be used, including a universal indicator dye that exhibits color changes across the entire acid-base pH spectrum.

The chemical indicating dye 78 may be selected based on the intended prey of the hunter. The stomach pH of herbivores is typically around 4.5 (slightly acidic) while the stomach pH of carnivores and omnivores is typically between 1 and 3. By selecting a halochromic chemical compound that undergoes color transition during the anticipated pH range, the accuracy of the indicator 70 can be improved and optimized for the intended prey.

Applying the chemical indicating dye 78 to the substrate 72 may be accomplished by treating the entire substrate or by selectively applying the indicating dye 78, such as by a printer, to form indicia 80 that provide clearer instruction (words) indicating a gut shot. The indicia 80 preferably blends into the background of the substrate and then becomes visible upon contact with acidic fluids, such as those present in a digestive tract. The indicating dye 78 may be incorporated in a neutral carrier solution (e.g., water) to enable the strength of the indicating dye to be altered. Dilution of most indicating dyes enables the indication reaction to occur while reducing the amount of indicating dye necessary to create the indicator. The viscosity of the indicator dye may also be altered to permit application to substrates using known printing technologies. Use of glycerin to adjust the viscosity of the indicating dye 78 has been proven to allow application of the indicating dye 78 to paper substrates using computer ink-jet printing technology.

The fletching 50 may also be configured to function as the indicator substrate 72 and retain sufficient chemical indicating dye 78 to exhibit the desired color change. Other substrate materials may also provide sufficient durability to permit a more permanent affixation to the arrow shaft and re-application of the indicating dye following use. Once used, the substrate 72 may be rinsed, the indicator fluid 78 reapplied, and the arrow is ready for reuse.

Figure 2:
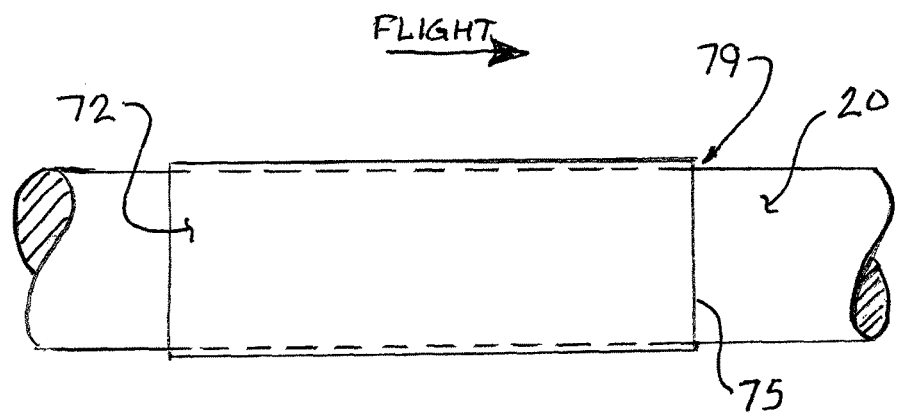
FIG. 2 provides a detail for one embodiment of an arrow shaft in which the shot indicator of the present invention is affixed to a conventional arrow shaft.

FIG. 2 illustrates one method for affixing the substrate 72 to the arrow shaft 20. The substrate is preferably adhesively affixed to the exterior surface of the shaft an adhesive 79. The adhesive may be separately applied prior to application of the substrate 72 or may be integrated on the inner surface of the substrate, commonly referred to as self-adhesive. The substrate 72 protrudes outside of the outer diameter of the shaft 20. As the thickness of the substrate is on the order of the thickness of a sheet of paper, the substrate protrudes less than 1 mm from the surface of the shaft 20 which testing has shown to have little to no effect on arrow flight.

Figure 3:
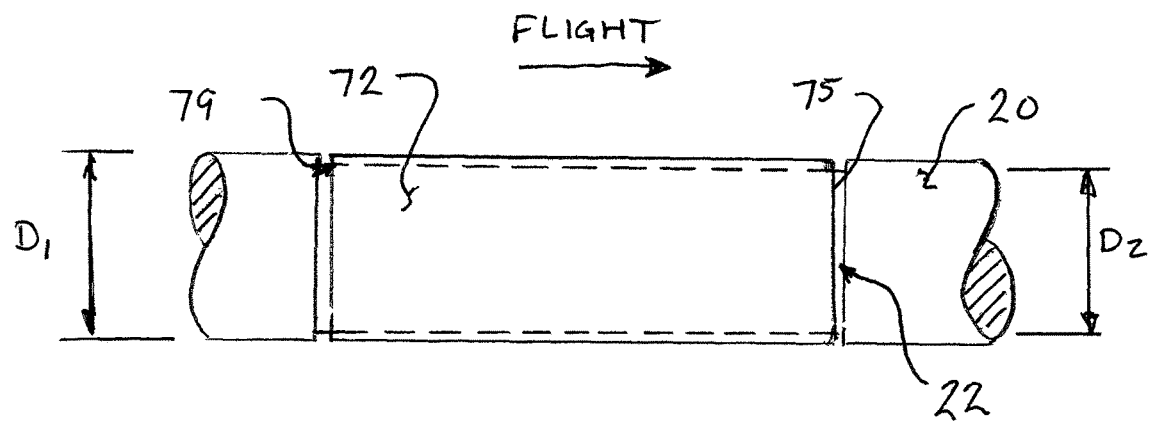
FIG. 3 provides a detail of an arrow shaft that has been modified to receive the indicator of the present invention.

The externally affixed substrate of FIG. 2 enables any conventional arrow or bolt to be modified to include a chemical shot indicator as easily as adhesively affixing one or more indicators to the arrow shaft. In FIG. 3, a modified arrow shaft 20 is shown comprising a receptacle 22 formed in the shaft 20. The receptacle 22 extends around the circumference of the shaft 20 and features a diameter $D_2$ that is slightly less than the shaft diameter $D_1$, ideally twice the thickness of the substrate 72 so that, when affixed, the outer surface of the substrate 72 will have an outer diameter similar to the outer diameter of the shaft adjacent to the receptacle and the substrate will be positioned flush with the rest of the arrow shaft. An adhesively affixed substrate is preferred to enable easy reuse of the arrow. Adhesive 79 properties for the receptacle application shown in FIG. 3 may be less than required for the FIG. 2 example as the leading end 75 is protected by the receptacle 22 and less prone to detachment from the shaft as the arrow passes through the target.

It will be understood that changes in the details, materials, steps and arrangements of parts which have been described and illustrated to explain the nature of the invention will occur to and may be made by those skilled in the art upon a reading of this disclosure within the principles and scope of the invention. The foregoing description illustrates the preferred embodiment of the invention; however, concepts, as based upon the description, may be employed in other embodiments without departing from the scope of the invention.

What is claimed is:

1. An arrow comprising:
    an elongate shaft having an exterior surface; and
    a chemically reactive indicator affixed to the exterior surface, the indicator visually displaying a first color and configured to visually display a second color only when subjected to a fluid having a pH value substantially less than 7.

2. The arrow of claim 1, wherein the indicator comprises a substrate and an indicating dye applied to the substrate, the indicating dye being chemically reactive with acidic fluids to turn from the first color to the second color.

3. The arrow of claim 2, wherein the indicating dye is a halochromic chemical compound.

4. The arrow of claim 3, wherein the halochromic chemical compound is selected based on digestive tract pH value of intended prey.

5. The arrow of claim 3, wherein the halochromic chemical compound is selected from the group comprising nitrazine yellow, lacmoids, methyl red, and bromothymol blue.

6. The arrow of claim 2, wherein the indicator further comprises an indicia formed by selective application of the indicating dye to a portion of the substrate, the indicia appearing in a second color compared to the first color of the remainder of the substrate when the indicating dye is exposed to acidic fluids allowing the indicia to be perceived.

7. The arrow of claim 2, wherein the arrow further comprises fletchings configured to guide the arrow during flight and the fletching is the substrate.

8. The arrow of claim 1, wherein the indicator is a litmus paper.

9. The arrow of claim 1, wherein the indicator is removeably adhesively affixed to the shaft.

10. The arrow of claim 1, wherein the shaft further comprises a circumferential recess in the exterior surface configured to receive the indicator therein in a manner such that the indicator is flush with the exterior surface when affixed in the recess.

11. A method for determining whether an arrow has penetrated the digestive tract of an animal comprising the steps of:
    providing an arrow having an elongate shaft with a chemically reactive indicator affixed thereto, the indicator visually displaying a first color;
    shooting the arrow toward the animal such that it strikes and passes through the animal; and retrieving the arrow and inspecting the indicator, the indicator visibly displaying a second color that is different from the first color only upon being subjected to a fluid having a pH value substantially less than 7 indicative of interaction with the animal's digestive tract, the indicator otherwise visually displaying the first color.

12. The method of claim 11, further comprising the steps of:

determining based on the color of the indicator a time necessary for the animal to most likely succumb to wound; and initiating a search for the animal after it has most likely succumbed to the wound and is unable to further evade the search.

13. The method of claim 12, further comprising the steps of:

removing the indicator from the arrow following shooting of the animal;

providing a new indicator to be affixed to the arrow shaft; and affixing the new indicator to the arrow shaft in preparation for an upcoming shot.

14. The method of claim 11, wherein the indicator is removeably adhesively affixed to the shaft.

15. The method of claim 14, wherein the indicator is a litmus paper.

16. The method of claim 11, wherein the indicator comprises a substrate and an indicating dye applied to the substrate, the indicating dye being chemically reactive with acidic fluids to turn from the first color to the second color.

17. The method of claim 16, wherein the indicating dye is a halochromic chemical compound.

18. The method of claim 17, further comprising the steps of:

providing a re-usable substrate affixed to the arrow;

rinsing the substrate with a neutral solution after inspecting the arrow following the shot of the animal; and applying the indicating dye to the substrate in preparation for an upcoming shot.

* * * * *